United States Patent
Iwasaka et al.

(10) Patent No.: US 7,131,992 B2
(45) Date of Patent: Nov. 7, 2006

(54) STENT

(75) Inventors: Masayuki Iwasaka, Tama (JP); Hitoshi Ishikawa, Hachoji (JP); Jun Iwami, Fujinomiya (JP); Makoto Takahashi, Fujinomiya (JP)

(73) Assignees: Olympus Corporation, Tokyo (JP); Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/267,542

(22) Filed: Oct. 9, 2002

(65) Prior Publication Data

US 2003/0088309 A1 May 8, 2003

(30) Foreign Application Priority Data

Oct. 9, 2001 (JP) ............................. 2001-311746

(51) Int. Cl.
*A61F 2/06* (2006.01)

(52) U.S. Cl. ...................................... 623/1.13; 623/1.1

(58) Field of Classification Search ............... 623/1.11, 623/1.12, 1.23, 23.64–23.69, 1.13, 1.22, 623/1.32, 1.33
See application file for complete search history.

(56) References Cited

U.S. PATENT DOCUMENTS

| | | | |
|---|---|---|---|
| 3,562,820 A * | 2/1971 | Braun | 623/23.64 |
| 5,176,626 A | 1/1993 | Soehendra | |
| 5,383,928 A * | 1/1995 | Scott et al. | 623/1.12 |
| 5,443,458 A | 8/1995 | Eury | |
| 5,474,563 A | 12/1995 | Myler et al. | |
| 5,514,176 A | 5/1996 | Bosley, Jr. | |
| 5,676,685 A * | 10/1997 | Razavi | 606/194 |
| 5,735,892 A | 4/1998 | Myers et al. | |
| 5,762,625 A | 6/1998 | Igaki | |
| 5,865,723 A | 2/1999 | Love | |
| 6,059,823 A * | 5/2000 | Holman et al. | 623/1.15 |

FOREIGN PATENT DOCUMENTS

| | | |
|---|---|---|
| EP | 0 423 916 A1 | 4/1991 |
| JP | 8-196643 | 8/1996 |
| JP | 10-192411 | 7/1998 |
| WO | WO 92/11824 | 7/1992 |

OTHER PUBLICATIONS

The American Heritage Dictionary of the English Language, Third Edition, 1992 Houghton Mifflin Company.*

* cited by examiner

*Primary Examiner*—Thomas Barrett
(74) *Attorney, Agent, or Firm*—Scully, Scott, Murphy & Presser, P.C.

(57) ABSTRACT

A stent arranged in a stenosis portion of the intracavital has a deformable frame urged so as to expand in a radially outward direction thereof and a generally cylindrical film-like member which is removably mounted around an outer periphery of the frame and which is expandable and reducible in a radial direction thereof.

3 Claims, 5 Drawing Sheets

STENT

BACKGROUND OF THE INVENTION

1. Field of the Invention

The present invention relates to a stent that expands a lumen in the body.

2. Description of the Related Art

Methods of recovering a stent indwelled in the body are disclosed in Jpn. Pat. KOKAI Publication No. 10-192411 and U.S. Pat. No. 5,474,563. With these methods, the opposite ends of the stent are pulled in the axially opposite directions thereof, respectively, to contract the stent in its radial direction so that the stent can be recovered from a lumen in the body. Further, EP No. 423916 discloses a method of contracting a trailing end of the stent in its radial direction to pull it out for recovery.

In particular, constriction of a lumen in the pancreatic and bile duct system often occurs as a result of an ulcer. If the stent is indwelled in a lumen in such a site for a long time, mucosa in the lumen may engross through stitches of the stent or the like or the stent may adhere to the mucosa.

Thus, to recover the indwelling stent, it must be released from the mucous membrane. Accordingly, it is conventionally difficult to recover the stent.

Further, if the indwelling stent is of a self expanding type, it is pressed against the mucosa in the lumen. Consequently, it is conventionally difficult to pull the stent out for recovery without damaging the mucosa in the lumen.

BRIEF SUMMARY OF THE INVENTION

The present invention provides a stent that can be easily recovered from a lumen.

According to an aspect of the invention, a stent arranged in a constricted portion of a coelom comprises a deformable frame which is urged so as to expand in a radially outward direction thereof in an installed state, and a generally cylindrical film-like member which is removably mounted around an outer periphery of the frame and which can be expanded or contracted in a radial direction thereof.

Additional advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the embodiments given below, serve to explain the principles of the invention.

DETAILED DESCRIPTION OF THE INVENTION

Figure 1A:
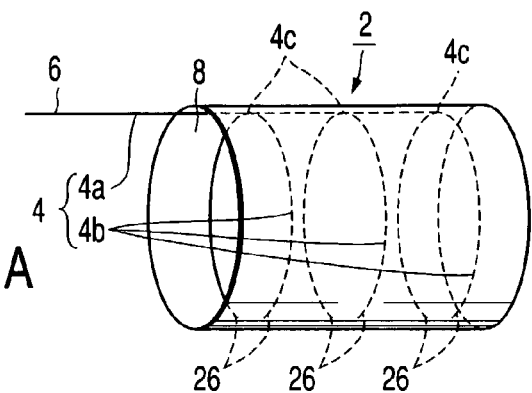
FIG. 1A is a schematic view showing a stent expanded in a lumen in the body.

Preferred embodiments of the present invention will be described below with reference to the drawings.

First, a first embodiment will be described with reference to FIGS. 1 to 3.

As shown in FIGS. 1A to 1D, a stent 2 according to this embodiment includes a frame 4 having a stem frame 4a that extends linearly in an axial direction of the stent 2 and a plurality of branch frames 4b that cross the stem frame 4a.

The stem frame 4a is composed of elastic material, preferably super-elastic alloy material, and can be freely bent. Preferably, other materials for the stem frame 4a have a high pullout force resistance, for example, metal wire, polyamide-based synthetic fiber thread, or silk thread. The branch frames 4b are formed of C-shaped springs composed of an elastic material, preferably a super-elastic alloy material. Each of the branch frames 4b can be freely reduced in its radially inward direction so that its opposite ends cross each other. The branch frame 4b also has an expanding force and can thus expand in its outward direction.

The stem frame 4a is connected to a central portion of each branch frame 4b by a connection section 4c so as not to fall out. The branch frames 4b are arranged in parallel at arbitrary intervals so as to extend in the same direction from a leading end to a trailing end of the stem frame 4a. The branch frames 4b are deformed not only in a circumferential direction of the C-shaped branch frames 4b but also in the axial direction of the stem frame 4a, using the respective connection sections 4c as fulcrums. The stem frame 4a has a root portion 6 located at a position that is more proximal than that of the branch frame 4b arranged closest to the trailing end of the stem frame 4a.

A part of the stent 2 in which the branch frames 4b are arranged in parallel is covered with a cylindrical film-like member 8, thereby forming the stent 2. Preferably, the film-like member 8 is thin and tear-resistant, and is preferably an elastic resin such as a silicone-based resin or urethane-based resin, or an organic material. The film-like member 8 can be freely expanded and reduced in its radial direction so as to follow the radial expansion and reduction of the branch frames 4b, respectively. The film-like member 8 can be freely installed on and removed from the frame 4.

To indwell the stent 2 in a stenosis portion 16 of a lumen in the body, for example, a stent delivery system 14 is used in a manner described below. The stent delivery system 14 includes an inner catheter 11 having a semispherical projecting portion 11a at a tip thereof and an outer sheath 13 covering the periphery of the inner catheter 11. The projecting portion 11a has substantially the same outer diameter as that of the outer sheath 13. Preferably, the projecting portion 11a has a through-hole 11b into which the inner catheter 11 is inserted and through which a guide wire or the like (not shown) can be inserted and fed forward. The outer sheath 13 can be moved along the axial direction of the inner catheter 11 relative to the inner catheter 11.

Figure 2A:
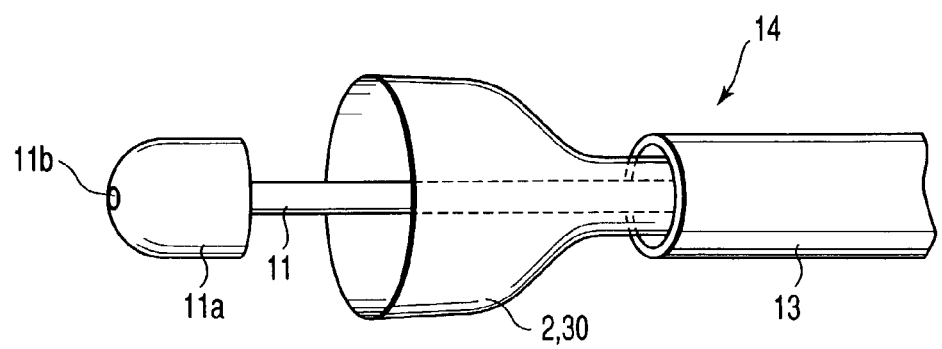
FIG. 2A is a schematic view showing a stent delivery system.

The stent 2 is held between an outer periphery of the inner catheter 11 and an inner periphery of the outer sheath 13 by having its diameter reduced. The root portion 6 of the stem frame 4a is arranged closer to the trailing end of the stent delivery system 14. As shown in FIGS. 3A and 3C, when the stent 2 is disposed in the stent delivery system 14, the branch frames 4b of the stent 2 each have their diameters reduced, with the opposite ends of each branch frame 4b crossing each other. With a leading end of the stent 2 thus disposed close to the projecting portion 11a, when the outer sheath 13 is pulled toward a practitioner relative to the inner catheter 11, the stent 2 self-expands gradually from the leading end to the trailing end, as shown in FIGS. 2A and 2B.

Figure 2B:
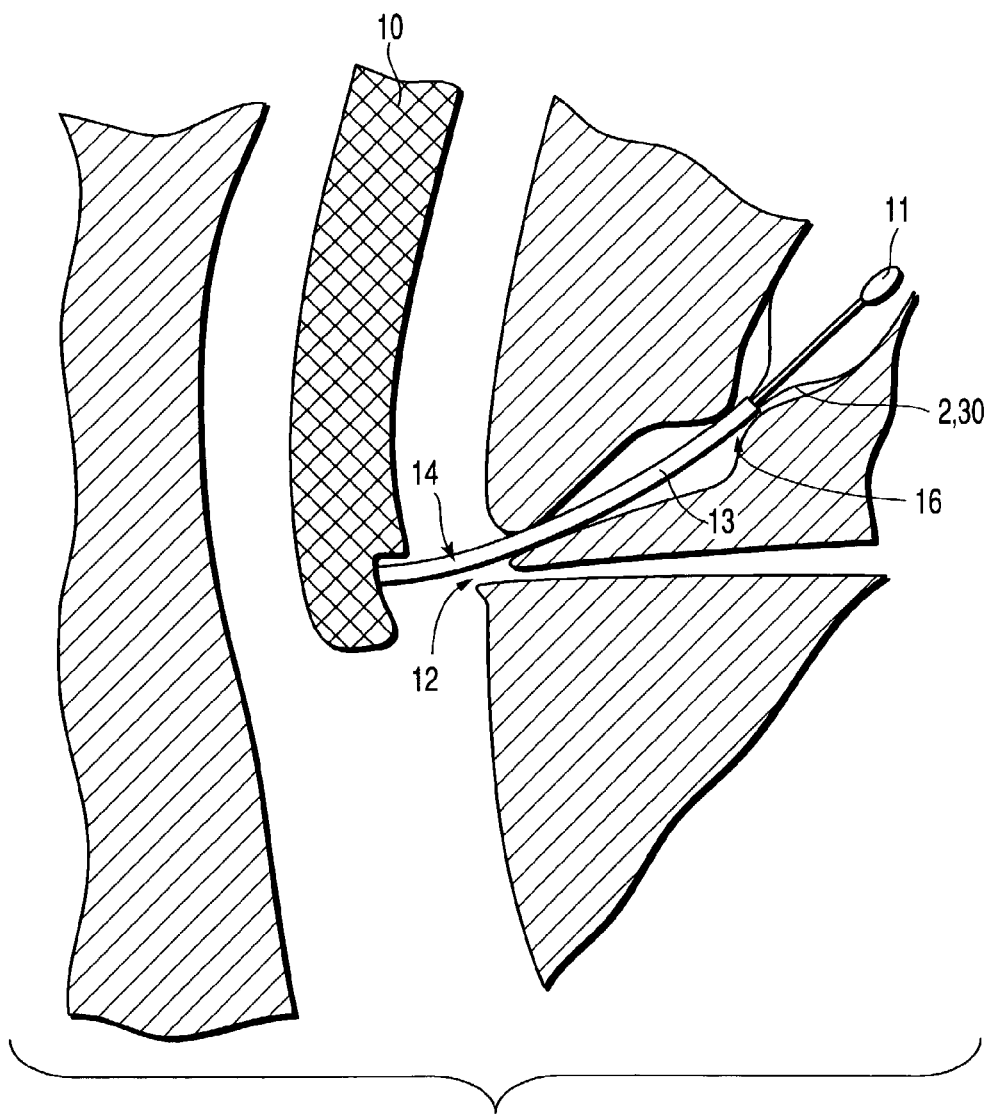
FIG. 2B is a schematic view showing that the stent shown in FIG. 1A has been orally fed using an endoscope to reach the duodenal papilla.
Figure 3A:
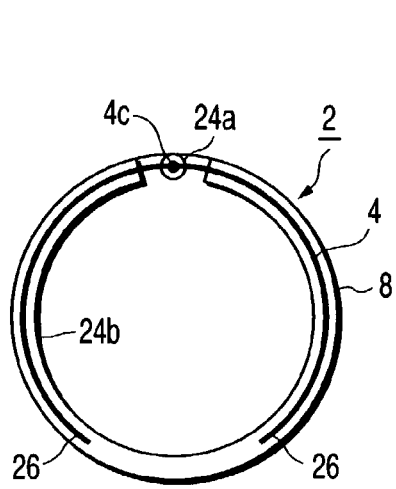
FIG. 3A is a sectional view taken along a circumference of the stent and showing that the stent has expanded in its radial direction.

As shown in FIG. 2B, the stent delivery system 14 with the stent 2 thus installed therein is orally fed until it reaches the duodenal papilla using, for example, a side-viewing endoscope 10. Then, the projecting portion 11a of the stent delivery system 14 is introduced into the inside of the stenosis portion 16. The stent 2, installed in the stent delivery system 14, is then introduced slightly into an anterior side of the stenosis portion 16 of the lumen.

With the stent 2 arranged on the anterior side of the stenosis portion 16, when the outer sheath 13 of the stent delivery system 14 is pulled toward the practitioner relative to the inner catheter 11, the stent 2 self-expands sequentially in a radially outward direction of the lumen starting with its leading end to sequentially expand the stenosis portion 16. Then, the outer sheath 13 is further pulled to allow the stent 2 to expand up to its trailing end, thereby expanding the stenosis portion 16. The expanded stent 2 is further inserted through the lumen. Subsequently, the inner catheter 11 is removed by pulling it toward the practitioner through a bore in the stent 2. Thus, when the stent 2 is released from the stent delivery system 14, it self-expands sequentially in the radially outward direction of the lumen starting with its leading end. The stent 2 is thus indwelled in the lumen with the stenosis portion 16 expanded. Accordingly, the stent 2 is expanded in the lumen in the radial direction of the lumen and pressed against an inner wall (mucosa) of the lumen as shown in FIG. 1A.

Now, a process of recovering the thus expanded stent 2 will be described. As shown in FIG. 1A, the root portion 6 of the stem frame 4a of the stent 2 is pulled toward the practitioner by gripping it using, for example, a gripping forceps or snare (not shown) introduced via the endoscope 10, shown in FIG. 2B.

Figure 1B:
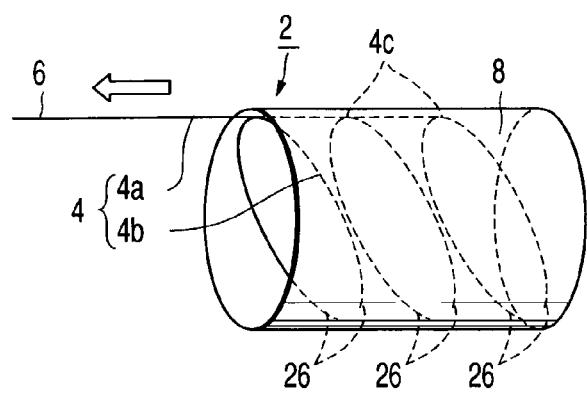
FIG. 1B is a schematic view showing how a frame of the stent shown in FIG. 1A is pulled out toward a practitioner.

Then, as shown in FIG. 1B, the connection sections 4c are tilted toward the practitioner relative to opposite ends 26 of each frame, which remain at the same positions. At this time, the branch frames 4b are deformed so as to correspond to the internal shape of the film-like portion 8, i.e. the shape of the stenosis portion 16.

Figure 1C:
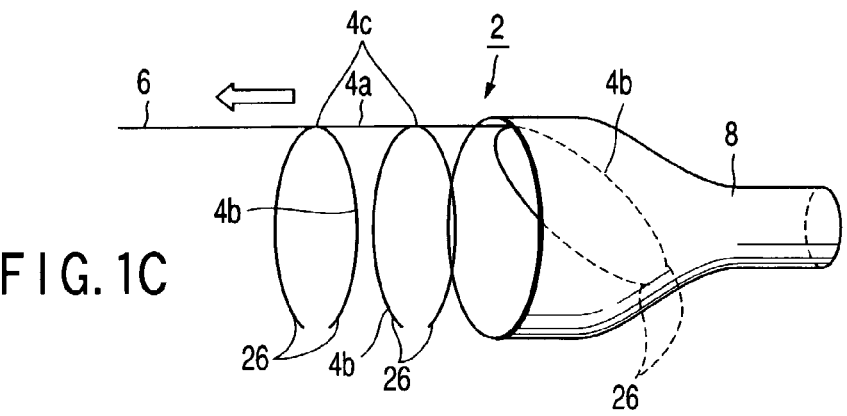
FIG. 1C is a schematic view showing that the frame of the stent shown in FIG. 1B has been pulled out further toward the practitioner.

When the stem frame 4a is further pulled out, the ends 26 of the branch frames 4b are moved toward the practitioner from the position at which the ends are arranged in an indwelling manner, against the frictional force between the branch frames 4b and the film-like member 8, as shown in FIG. 1C. Then, the branch frames 4b are sequentially pulled out from the film-like member 8 starting with the one arranged closest to the root portion 6. As the frame 4 is moved, the film-like member 8 gradually loses its expanding force starting with its leading end (located on the inside of the stenosis portion 16), and is reduced in its radial direction. Thus, the film-like member 8 is sequentially released from the mucosa in the lumen starting with a part thereof which has been reduced in its radial direction.

Figure 1D:
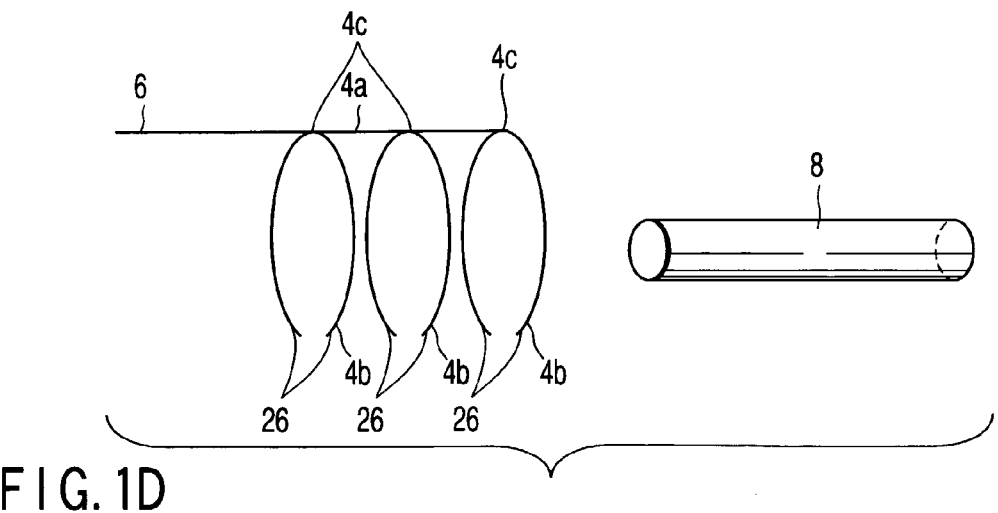
FIG. 1D is a schematic view showing that the frame of the stent has been pulled out and that the frame and a film-like member have been separated from each other.

Then, once the frame 4 is completely pulled out of the film-like member 8 as shown in FIG. 1D, the film-like member 8 completely loses its expanding force and is reduced in its radial direction. The film-like member 8 is thus released from the mucosa in the lumen.

Subsequently, the frame 4 is recovered by entirely pulling it out through, for example, a channel in the endoscope 10. Furthermore, the film-like member 8, which has lost its expanding force, is similarly recovered using, for example, the gripping forceps.

Accordingly, to recover the stent 2 indwelled in the stenosis portion 16 of the lumen or the like as described in this embodiment, only the frame 4 is first recovered. The frame 4 does not contact directly the mucosa in the lumen and is thus prevented from being buried in the mucosa or adhering thereto. That is, the frame 4 can be easily removed from the lumen. Thus, the film-like member 8 of the stent 2 is easily released from the mucosa in the living body for recovery. Furthermore, at least in the initial stage of the operation of pulling out the frame 4, the frame 4 is unlikely to rub the mucosa in the lumen and thus reduces damage thereto.

As shown in FIG. 1, the frame 4 in this embodiment includes the stem frame 4a and the branch frames 4b. However, the present invention is not limited to these frames 4a and 4b. For example, frames with other shapes may be used provided that the frame 4, which has an expanding force exerted in its radial direction, and the film-like member 8, which directly contacts the mucosa, can be separated from each other for recovery. Thus, the frame 4 may have a knitted or textile structure or a networked structure called "expanded metal" (also referred to as "metal lath") in which a cut is made in a pipe-like member in its axial direction so as to mechanically increase its diameter.

Further, the root portion 6 of the stem frame 4a may be located inside the duodenal papilla 12 as shown in FIG. 2B or may reach the duodenum so as to allow checks to be carried out using the endoscope 10. Furthermore, the root portion 6 of the stem frame 4a may have a ball (not shown) installed thereon and having a larger diameter than the root portion 6 so that sufficient pullout force can be exerted on the gripping forceps or the like when both root portion 6 and ball are gripped by the gripping forceps or the like.

Now, a second embodiment will be described with reference to FIGS. 4 and 5. This embodiment is a variation of the first embodiment. The same members as those in the first embodiment are denoted by the same reference numerals. Description of these members is omitted.

In this embodiment, as shown in FIGS. 3 and 4, the film-like member 8 has a lumen section 24 having a substantially tubular structure and formed on an inner wall of the film-like member as a support mechanism for supporting the frame 4, urged in its radially outward direction.

As shown in FIG. 3A, the film-like member 8 is provided, on its inner wall, with a first lumen section 24a extending along the axial direction of the stent 2 to form a conduit for the stem frame 4a and a second lumen section 24b extending normal to the first lumen section 24a and along a circumferential direction of the film-like member to form a conduit for the branch frames 4b. The first lumen section 24a has a cut (not shown) extending along its axial direction and into and out of which the stem frame 4a can be moved. Preferably, this cut is formed at 180° to the position at which the first lumen section 24a is attached to the film-like member 8. Of course, the cut may be formed at any position except the one at which the first lumen section 24a is attached to the film-like member 8. The second lumen section 24b expands and reduces in its axial direction, i.e. in the radial direction of the film-like member 8. Thus, as the second lumen section 24b expands or reduces, it expands or reduces in the axial direction of the second lumen section 24b.

Further, the second lumen section 24b is shaped like the character C. Thus, a space is formed between the first lumen section 24a and second lumen section 24b for inserting therein or pulling therefrom the ends 26 of the branch frames 4b. Consequently, the stent 2 is formed by setting the frame 4 in the film-like member 8, i.e. inserting the stem frame 4a into the first lumen section 24a through the cut in the first lumen section 24a, and sequentially inserting the branch frames 4b into the second lumen section 24b through the space between the first lumen section 24a and the second lumen section 24b.

Figure 4A:
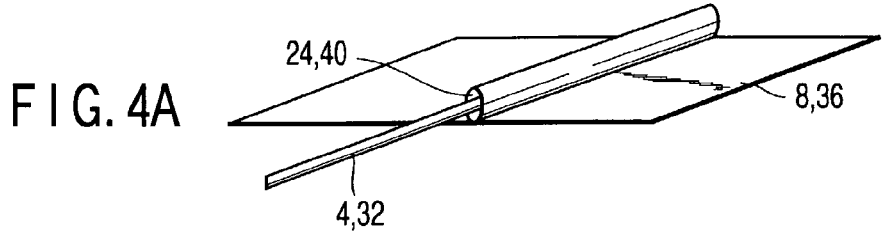
FIG. 4A is a schematic view showing that the frame has been inserted into a lumen section installed on an inner wall of the film-like member.
Figure 4B:
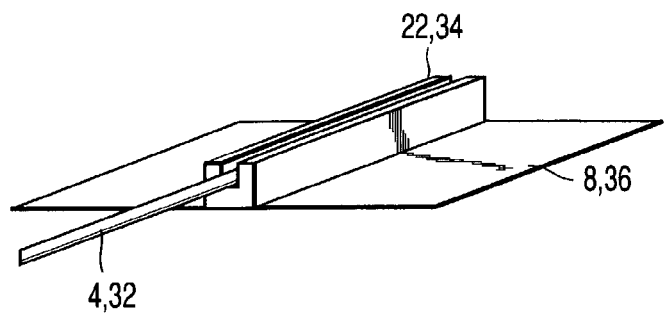
FIG. 4B is a schematic view showing that the frame has been inserted into a rail section installed on the inner wall of the film-like member.

As shown in FIG. 4B, the film-like member 8 of the stent 2 may be provided, on its inner wall, with a support mechanism in place of the above described lumen section 24, the support mechanism having a recess surface portion 22 formed therein, which has a rectangular cross section and in which the frame 4 is disposed. The recess surface portion 22, like the lumen section 24, is formed so as to expand and reduce.

Figure 3B:
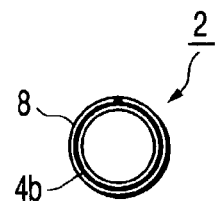
FIG. 3B is a sectional view taken along a circumference of the stent and showing that the stent had contracted in its radial direction.
Figure 3C:
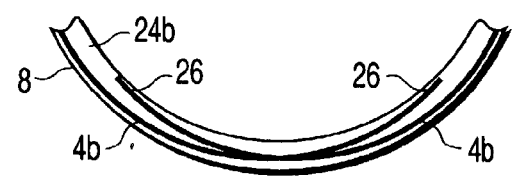
FIG. 3C is a partial sectional view showing a part of the stent in which ends of the frame shown in FIG. 3B cross and overlap each other.

The stent 2 configured as described above is indwelled in the stenosis portion 16 of the lumen as described in the first embodiment. To install the stent 2 in the stent delivery system 14, the inner catheter 11 of the stent delivery system 14, shown in FIG. 2A, is inserted into the bore in the stent 2, i.e. into the branch frames 4b. Subsequently, as shown in FIG. 3B and enlargedly in FIG. 3C, the stent 2 is installed so that its outer periphery urges an inner wall of the outer sheath 13 in the radially outward direction. Thus, the opposite ends 26 of each branch frame 4b cross each other, with the film-like member 8 and the second lumen section 24b reducing.

Then, as described in the first embodiment, the stent 2 is released from the stent delivery system 14 (see FIG. 2A). Then, as shown in FIG. 2B, the stent 2 self-expands in its radial direction to expand the stenosis portion 16 of the lumen.

Now, a process of recovering the stent 2. The root portion 6 of the stem frame 4a is pulled toward the practitioner by gripping it using, for example, the gripping forceps or snare (not shown) introduced via the endoscope 10, shown in FIG. 2B.

Then, the stem frame 4a is pulled toward the root portion 6 along the first lumen section 24a. Following this operation, the branch frames 4b, arranged in parallel, are pulled out of the second lumen section 24b through the vicinities of the corresponding connection sections 4c. The branch frames 4b pulled out of the second lumen section 24b are moved toward the practitioner while being bent toward the practitioner.

As the stem frame 4a is further pulled out along the first lumen section 24a, the opposite ends 26 of the branch frames 4b are pulled out of the second lumen section 24b. The film-like member 8 gradually loses its expanding force starting with its leading end, and is reduced in its radial direction. Thus, the film-like member 8 is sequentially released from the mucosa in the lumen starting with a part thereof which has been reduced in its radial direction.

Accordingly, to recover the stent 2 indwelled in the stenosis portion 16 of the lumen or the like as described in this embodiment, only the frame 4 is first recovered. The frame 4 does not directly contact the mucosa in the lumen and is thus prevented from being buried in the mucosa or adhering thereto. That is, the frame 4 can be easily removed from the lumen. Thus, the stent 2 is easily released from the mucosa for recovery. Furthermore, at least in the initial stage of the operation of pulling out the frame 4, the frame 4 is unlikely to rub the mucosa in the lumen and thus reduces damage thereto. Further, in this embodiment, the frame 4 is expanded and reduced along the lumen section 24. This is particularly effective in reducing the stent 2 before installing it in the outer sheath 13 or the like compared to the first embodiment.

Figure 5A:
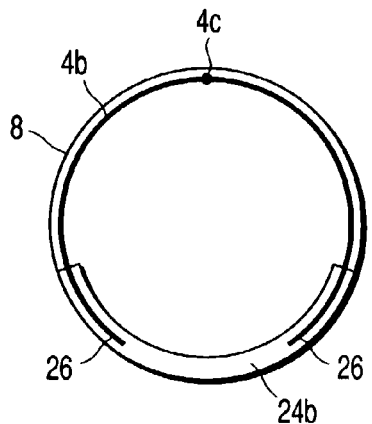
FIG. 5A is a sectional view taken along a circumference of the stent and showing how the rail section or lumen section is continuously installed over substantially half the circumference of the stent.
Figure 5B:
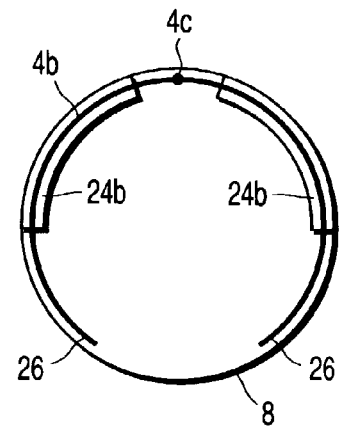
FIG. 5B is a sectional view taken along a circumference of the stent and showing how the rail section or lumen section is discontinuously installed over half the circumference of the stent.

For example, the second lumen section 24b may be arranged around only substantially half the circumference of the film-like member 8 so as to continuously cover the vicinity of the ends 26 of the branch frames 4b as shown in FIG. 5A. Alternatively, the second lumen section 24b may be discontinuously arranged around only substantially half the circumference so as to cover two quarters of the circumference of the film-like member 8 as shown in FIG. 5B. Alternatively, the second lumen section 24b may be arranged around substantially all the circumference along the branch frame 4b as shown in FIG. 3A, described above.

Further, the recess surface portion 22 may be arranged similarly to any of the lumen sections 24 shown in FIGS. 3 and 5. The first lumen section 24a, which holds the stem frame 4a as shown in FIG. 5, may be omitted.

Figure 4C:
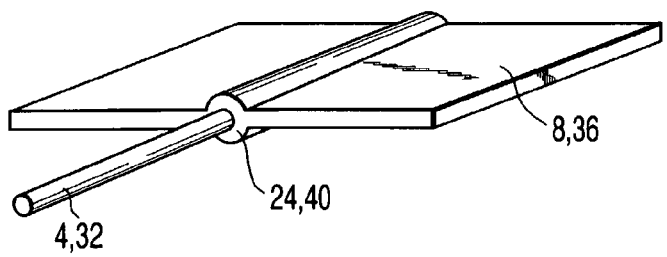
FIG. 4C is a schematic view showing that the frame has been inserted into a lumen section provided inside the film-like member.

Furthermore, the lumen section 24 may not be provided on the inner wall of the film-like member 8, as shown in FIGS. 4A and 4B. Alternatively, the frame 4 may be held so as to penetrate the interior of the film-like member 8, as shown in FIG. 4C.

Now, a third embodiment will be described with reference to FIG. 6. As shown in FIGS. 6A to 6C, a stent 30 according to this embodiment is provided of one frame 32 made of a shape memory alloy to memorize a substantially linear shape thereof assumed in a no-load state, and a cylindrical film-like member 36 having a spiral rail section 34 (see FIG. 4B) on an inner wall portion thereof. The film-like member 36 can be expanded and reduced in its radial direction. When the frame 32 is inserted into the rail section 34, the film-like member 36 is expanded in its radially outward direction. Following the expansion of the film-like member 36, the rail section 34 is similarly expanded in its radially outward direction.

The rail section 34, like the recess surface portion 22, shown in FIG. 4B and described above, has a recess surface with a rectangular cross section and supports the frame 32. As shown in FIG. 6A, the rail section 34 allows the frame 32 to be introduced into the film-like member 36 while guiding the frame 32 so that the frame 32 is spirally deformed, thereby expanding the rail section 34 in its radially outward direction. A leading end of the frame 32 is locked by a locking section (not shown) provided at a leading end of the rail section 34. A trailing end of the frame 32 extends to the outside of the rail section 34, i.e. beyond the rear end of the film-like member 36.

The stent 30, like the stent 2, described in the first and second embodiments, is held between the outer periphery of the inner catheter 11 and the inner periphery of the outer sheath 13 while having its diameter reduced. A root portion 38 of the frame 32 is arranged at the trailing end of the stent delivery system 14. When the stent 30 is disposed in the stent delivery system 14, the frame 32 of the stent 30 has its diameter reduced and extends longer toward the practitioner than in the case in which root portion 38 of the frame 32 is expanded. In the state where a leading end of the stent 30 is thus disposed close to the projecting portion 11a, when the outer sheath 13 is pulled toward the practitioner relative to the inner catheter 11, the stent 30 self-expands gradually from leading end to trailing end thereof as shown in FIGS. 2A and 2B.

The stent delivery system 14 indwells the stent 30 in the stenosis portion 16 as in the case with the stent 2, described in the first and second embodiments.

Now, a process of recovering the stent 30 will be described. The root portion 38 of the frame 32 of the stent 30 is pulled toward the practitioner by gripping it using, for example, the gripping forceps or snare (not shown) introduced via the endoscope 10, shown in FIG. 2B.

Figure 6A:
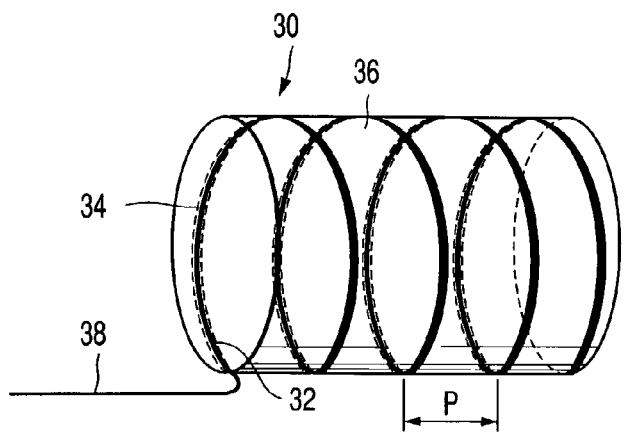
FIG. 6A is a schematic view showing that the stent has expanded in the lumen.
Figure 6B:
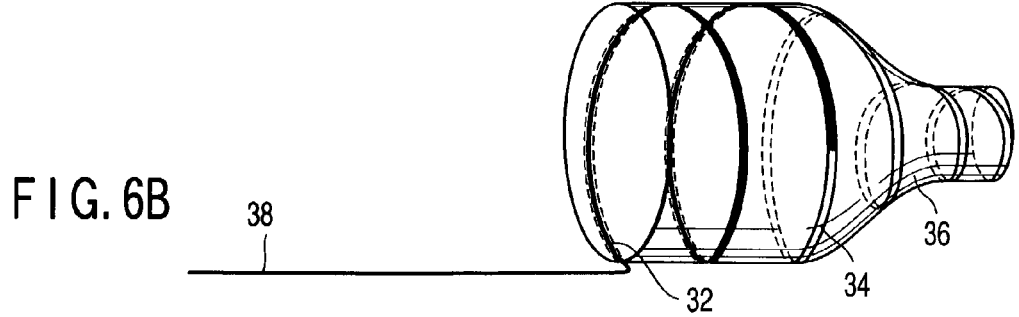
FIG. 6B is a schematic view showing how the stent shown in FIG. 6A is pulled out toward the practitioner.

As shown in FIG. 6B, the frame 32 is sequentially pulled along the rail section 34 starting with a part thereof which corresponds to a leading end of the film-like member 36. The film-like member 36, out of which the frame 32 has been pulled, sequentially loses its expanding force starting with its leading end, and is reduced in its radially inward direction. Thus, the film-like member 36 is sequentially released from the mucosa starting with a part thereof which has been reduced.

Figure 6C:
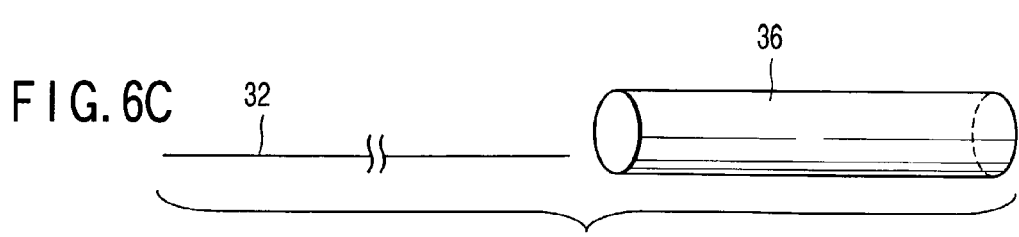
FIG. 6C is a schematic view showing that the frame of the stent has been pulled so as to separate the frame from the film-like member.

Once the frame 32 has been completely pulled out of the stent 30, it is released from the rail section 34, becomes substantially linear, and is easily taken out of the body as shown in FIG. 6C. Furthermore, the film-like member 36, out of which the frame 32 has been pulled, loses its expanding force that causes itself to expand in its radially outward direction. Consequently, the film-like member 37 is easily released from the mucosa and easily recovered from the lumen similarly to the film-like member 8, described in the first and second embodiments.

Thus, to recover the stent 30, indwelled in the stenosis portion 16 of the lumen or the like as described in this embodiment, only the frame 32 is first recovered. At this time, the frame 32 does not directly contact the mucosa in the lumen and is thus prevented from being buried in the mucosa or adhering thereto. That is, the frame 32 can be easily removed from the lumen. Thus, the film-like member 36 of the stent 30 is easily released from the mucosa for recovery. Further, the frame 32 memorizes its linear shape and is easily bent so as to correspond to the internal shape of the body. As a result, the frame 32 can be easily recovered to further reduce the patient's pain.

In this embodiment, the rail section 23 supports the frame 32 as shown in FIG. 6A. However, for example, a lumen section 40 may be provided in place of the rail section 34 as shown in FIGS. 4A and 4C, so as to support the frame 32 in a fashion wrapping it. This prevents the frame 32 from being derailed, thereby allowing the frame 32 to be reliably supported compared to the rail section 34.

Now, a fourth embodiment will be described with reference to FIG. 7. This embodiment is a variation of the third embodiment. The same members as those in the third embodiment are denoted by the same reference numerals. Description of these members is omitted.

Figure 7:
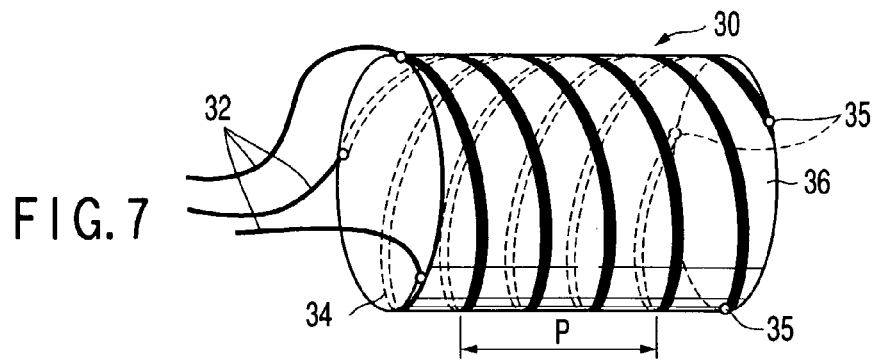
FIG. 7 is a schematic view showing a stent having a plurality of frames installed along a rail section provided on the inner wall of the film-like member.

As shown in FIG. 7, the stent 30 according to this embodiment is provided of a plurality of (in this embodiment, three) frames 32 made of shape memory alloy so as to memorize a generally linear shape thereof, and the cylindrical film-like member 36 having a plurality of (in this embodiment, three) spiral rail sections 34 on the inner wall portion thereof. The film-like member 36 can be expanded in its radial direction. When the frames 32 are sequentially inserted into the rail section 34, they exert a reaction force to return to their original state, thereby expanding the stent 30 in its radially outward direction. Following the expansion of the film-like member 36, the rail section 34 is similarly expanded in its radially outward direction. The leading ends of the frames 32 are locked by an engagingly locking section 35 provided at the leading end of the rail section 34. The trailing end of the frame 32 extends to the outside of the rail section 34.

If the stent 30 is indwelled in the stenosis portion or the like, a process is executed which is similar to the one described in the third embodiment.

To recover the stent 30, the plurality of frames 32 are pulled toward the practitioner one by one using an instrument inserted into the channel in the endoscope 10, and are thus sequentially pulled out of the film-like member 36. For example, when one of the frames 32 has been pulled out, the radially outward urging force of the stent 30 is weakened. However, the state in which the outward expanding force is retained, i.e. the expanded state is maintained. Further, when two of the frames 32 have been pulled out, the radially outward urging force is further weakened. However, the outward expanded state is maintained. When the final frame 32 has been pulled out, the stent 30 sequentially loses its expanding force starting with its leading end. The stent 30 has its diameter reduced and is thus released from the mucosa.

Accordingly, the stent 30 according to this embodiment allows a larger pitch P to be set for the spirals of the frames 32 than the stent 30 shown in FIG. 6 and described in the third embodiment. Consequently, the frames 32 can be easily installed in the film-like member 36 and can be more easily pulled out thereof. This facilitates recovery of the frames 32 to reduce the patient's pain during recovery.

Now, a fifth embodiment will be described with reference to FIG. 8. This embodiment is a variation of the third and fourth embodiments. The same members as those in the third and fourth embodiments are denoted by the same reference numerals. Description of these members is omitted.

Figure 8:
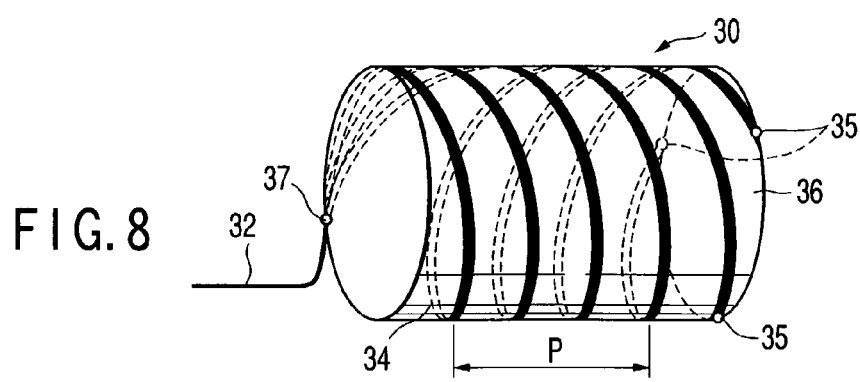
FIG. 8 is a schematic view showing a stent having a plurality of frames installed along a rail section provided on the inner wall of the film-like member, the frames being integrated together at a trailing end of the stent.

As shown in FIG. 8, the stent 30 according to this embodiment is provided of a plurality of frames 32 made of shape memory alloy so as to memorize a generally linear shape thereof, and the cylindrical film-like member 36 having a plurality of spiral rail sections 34 on the inner wall thereof. The film-like member 36 can be expanded in its radial direction. When the frames 32 are sequentially inserted into the rail section 34, the film-like member is expanded in its radially outward direction. Following the expansion of the film-like member 36, the rail section 34 is similarly expanded in its radially outward direction. The leading ends of the frames 32 are locked by the engagingly locking section 35 provided at the leading end of the rail section 34. The frames 32 are integrated together by a knot section 37 provided close to the trailing end of the rail section 34, and extend further toward the practitioner. When the stent 30 is arranged in the stent delivery system 14, the knot section 37 is separated from the trailing end of the film-like member 36 and lies closer to the practitioner.

To recover the stent 30, the plurality of frames 32, integrated together behind the knot section 37, are pulled together toward the practitioner using the instrument inserted into the channel in the endoscope 10. The stent 30 gradually loses its expanding force starting with its leading end. The stent 30 then has its diameter reduced and is released from the mucosa.

Accordingly, the number of operations required to pull out the frames 32 decreases compared to the recovery of the stent 30 shown in FIG. 7 and described in the fourth embodiment. This reduces the time and labor required for the operation to facilitate the recovery of the stent 30. Further, as in the case with the fourth embodiment, a larger pitch P can be set for the spirals of the frames 32 than the pitch P for the stent 30 described in the third embodiment. Consequently, the frames 32 can be easily installed in the film-like member 36 and can be more easily pulled out thereof. This facilitates recovery of the frames 32 to reduce the patient's pain during recovery.

In the third to fifth embodiments, the frames 32 need not always be spirally deformed. For example, the frames may have a knitted structure or may be formed by waved wiring so as to form a cylinder.

Figure 9A:
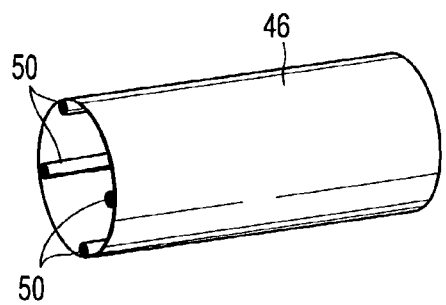
FIG. 9A is a perspective view showing a film-like member provided with a plurality of reinforcing members extending in an axial direction of the stent.
Figure 9B:
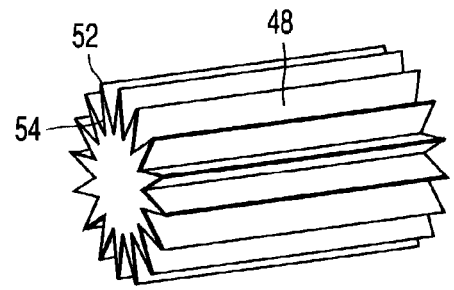
FIG. 9B is a perspective view showing a film-like member folded so as to form crests and troughs alternately repeatedly arranged in the axial direction of the stent.

The film-like members 8 and 36, shown in the first to fifth embodiments, are expanded following the radially outward expansion of the frames 4 and 32. However, the present invention is not limited to these frame members 8 and 36. For example, a film-like member 46 may be used which has one or more reinforcing members 50 provided thereon so as to extend in the axial direction of the stent as shown in FIG. 9A. Alternatively, a film-like member 48 may be used which is folded so as to form crest portions 52 and trough portions 54 alternately repeatedly arranged in the axial direction of the stent as shown in FIG. 9B. When the film-like members 46 and 48, shown in FIGS. 9A and 9B, respectively, are removed from the frame, they may be reduced in their radially inward direction. Alternatively, the film-like members 46 and 48 may be folded along the axial reinforcing members 50, shown in FIG. 9A or the crest portions 52 and trough portions 54, shown in FIG. 9B.

Thus, even if the film-like members 46 and 48 themselves are not directional, they may have non-compressibility in their axial direction and may be freely reduced and expanded or folded in their radial direction.

As described above, according to the first to fifth embodiments, in recovering the stent 2 or 30, the frame 4 or 32 is separated from the film-like member 8 or 36. Thus, the frame 4 or 32 can be recovered without taking special measures to prevent the frame being buried in or adhering to the mucosa. The film-like member 8 or 36 loses its expanding force and is thus easily recovered by releasing it from the mucosa.

These features facilitate recovery of the entire film-like member 2 or 30, while minimizing stimuli to the mucosa.

Therefore, the stents 2 and 30, shown in the embodiments, are particularly effective in indwelling in the lumen for a long time or in other cases.

Figure 10A:
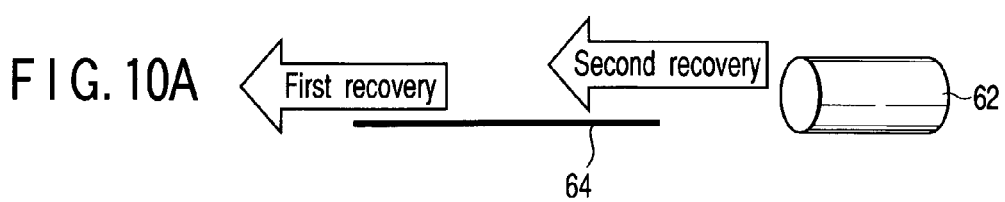
FIG. 10A is a schematic view useful in describing a stent recovery process.
Figure 10B:
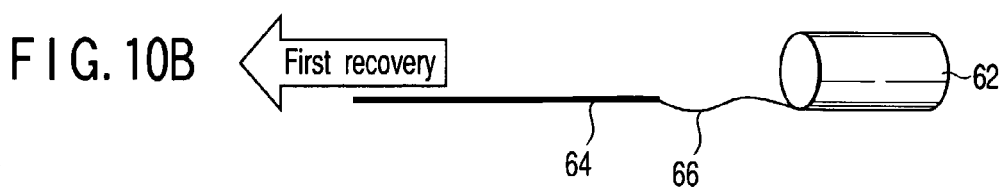
FIG. 10B is a schematic view useful in describing a variation of the stent recovery process.

The first to fifth embodiments have been described in such a manner that the stent is recovered by separating a film-like member 62 from a frame 64 as shown in FIG. 10A. However, the present invention is not limited to such a recovery process. For example, as shown in FIG. 10B, a part of the frame 64 is directly or indirectly connected to a part of the film-like member 62 using a connection member such as thread 66. Then, when the frame 64 is pulled out of the film-like member 62, the film-like member 62 is recovered together with the frame 64. This reduces the time and labor required to recover only the film-like member 62 after pulling out the frame.

The film-like member 62 may be made of bio-absorbable and biodegradable material, such as polymers of polylacic acid or polyglycolic acid. In this case, member 62 will be absorbed and decomposed in the living body after the frame 64 is removed from the living body. Thus, it is unnecessary to remove the frame 62 from the living body.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A stent for arrangement in a stenosis portion in an intracavital, the stent comprising:
    at least one deformable frame which is urged so as to expand in a radially outward direction thereof in an installed state, the frame having an inner surface, an outer surface, a proximal end and a distal end; and
    a cylindrical film-like member having an inner periphery defining a lumen for passage of a bodily fluid through the film-like member and an outer periphery, the inner periphery being removably mounted around the outer surface of the frame such that the inner surface is in communication with the lumen and the frame is capable of being withdrawn from the film-like member through the lumen, the film-like member being expandable and reducible in a radial direction thereof, the outer periphery of the film-like member being in tight contact with the stenosis portion when the film-like member is expanded in a radially outward direction thereof, the film-like member having a proximal end and a distal end;

wherein the frame is formed to be generally linear in a no-load state;

wherein the film-like member has a support mechanism inside the outer periphery of the film-like member, the support mechanism supporting at least a part of the frame when the distal end of the frame is arranged closer to the proximal end of the film-like member than to the distal end of the film-like member and when the proximal end of the frame is arranged at a position which is more proximal than the proximal end of the film-like member; and wherein the support mechanism is spirally formed on the film-like member.

2. A stent for arrangement in a stenosis portion in an intracavital, the stent comprising:

at least one deformable frame which is urged so as to expand in a radially outward direction thereof in an installed state, the frame having an inner surface, an outer surface, a proximal end and a distal end; and a cylindrical film-like member having an inner periphery defining a lumen for passage of a bodily fluid through the film-like member and an outer periphery, the inner periphery being removably mounted around the outer surface of the frame such that the inner surface is in communication with the lumen and the frame is capable of being withdrawn from the film-like member through the lumen, the film-like member being expandable and reducible in a radial direction thereof, the outer periphery of the film-like member being in tight contact with the stenosis portion when the film-like member is expanded in a radially outward direction thereof, the film-like member having a proximal end and a distal end;

wherein the frame is formed to be generally linear in a no-load state;

wherein the film-like member has a support mechanism inside the outer periphery of the film-like member, the support mechanism supporting at least a part of the frame when the distal end of the frame is arranged closer to the proximal end of the film-like member than to the distal end of the film-like member and when the proximal end of the frame is arranged at a position which is more proximal than the proximal end of the film-like member; and wherein the support mechanism has a rail section provided on the inner periphery of the film-like member and which supports the frame in a recess portion having an opening facing in a radially inward direction of the film-like member.

3. A stent according to claim 1, wherein the support mechanism has a rail section provided on the inner periphery of the film-like member and which supports the frame in a recess portion having an opening facing in a radially inward direction of the film-like member.

* * * * *